US012662476B2

(12) United States Patent
Wailes et al.

(10) Patent No.: US 12,662,476 B2
(45) Date of Patent: Jun. 23, 2026

(54) HERBICIDAL THIAZOLE COMPOUNDS

(71) Applicant: SYNGENTA CROP PROTECTION AG, Basel (CH)

(72) Inventors: Jeffrey Steven Wailes, Bracknell (GB); Zoe Jane Anderson, Bracknell (GB); Gordon Richard Munns, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 1018 days.

(21) Appl. No.: 17/776,331

(22) PCT Filed: Nov. 13, 2020

(86) PCT No.: PCT/EP2020/081994

§ 371 (c)(1),
(2) Date: May 12, 2022

(87) PCT Pub. No.: WO2021/094504

PCT Pub. Date: May 20, 2021

(65) Prior Publication Data

US 2022/0411417 A1 Dec. 29, 2022

(30) Foreign Application Priority Data

Nov. 15, 2019 (GB) ...................................... 1916676

(51) Int. Cl.

*C07D 417/12* (2006.01)
*A01N 43/78* (2006.01)
*A01P 13/00* (2006.01)

(52) U.S. Cl.

CPC ........... *C07D 417/12* (2013.01); *A01N 43/78* (2013.01); *A01P 13/00* (2021.08)

(58) Field of Classification Search

CPC .................................................... C07D 417/12
See application file for complete search history.

(56) References Cited

U.S. PATENT DOCUMENTS 4,973,599 A * 11/1990 Gilman ................ C07D 277/36 514/369

FOREIGN PATENT DOCUMENTS

| | | | |
|---|---|---|---|
| EP | 0262845 | A1 | 4/1988 |
| WO | 2015089003 | A1 | 6/2015 |
| WO | 2015108779 | A1 | 7/2015 |

OTHER PUBLICATIONS

CAS Registry 769087-26-5 (Oct. 25, 2004).*
Written Opinion of the International Searching Authority and International Search Report for PCT/EP2020/081994, mailed Apr. 16, 2021.
GB search report for GB1916676.8, date of search May 1, 2020.

* cited by examiner

*Primary Examiner* — Valerie Rodriguez-Garcia
(74) *Attorney, Agent, or Firm* — BakerHostetler; Toni-Junell Herbert

(57) ABSTRACT

The present invention relates to compounds of Formula (I), or an agronomically acceptable salt of said compounds wherein Q, $R^1$, $R^3$, $R^4$ and n are as defined herein. The invention further relates to herbicidal compositions which comprise a compound of Formula (I) and to the use of compounds of Formula (I) for controlling weeds, in particular in crops of useful plants.

(I)

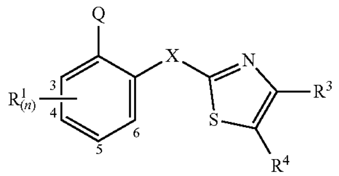

17 Claims, No Drawings

HERBICIDAL THIAZOLE COMPOUNDS

CROSS-REFERENCE TO RELATED APPLICATIONS

This application is a 371 National Stage application of International Application No. PCT/EP2020/081994 filed Nov. 13, 2020, which claims the benefit of GB 1916676.8, filed Nov. 15, 2019.

The present invention relates to novel herbicidal compounds, to processes for their preparation, to herbicidal compositions which comprise the novel compounds, and to their use for controlling weeds, in particular in crops of useful plants, or for inhibiting plant growth.

WO2015/108779 discloses pyrimidinyloxy benzene derivatives as herbicides. The present invention provides novel herbicidal compounds. Thus, according to the present invention there is provided a compound of Formula (I):

(I)

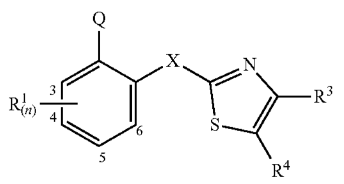

or an agronomically acceptable salt thereof,
wherein

Q is selected from the group consisting of $C_1$-$C_6$haloalkyl, $C_1$-$C_6$haloalkyl-C(O)—, $C_1$-$C_6$haloalkoxy-, $C_1$-$C_6$haloalkoxyC(O)— and a 5-membered aromatic heterocyclic ring which is optionally substituted by 1 or 2 $R^2$ substituents independently selected from the group consisting of $C_1$-$C_4$alkyl, $C_2$-$C_4$alkenyl, $C_2$-$C_4$alkynyl, cyclopropyl, $C_1$-$C_4$haloalkyl, $C_1$-$C_2$alkoxy-, $C_1$-$C_2$haloalkoxy-, halogen, —C(O)$C_1$-$C_4$alkyl, $NO_2$, —$CH_2$CN, —CN and —$S(O)_p$$C_1$-$C_4$alkyl;

X is O or $S(O)_p$;

each $R^1$ is independently selected from the group consisting of halogen, —CN, nitro, $C_1$-$C_4$alkyl, $C_2$-$C_4$alkenyl, $C_2$-$C_4$alkynyl, $C_1$-$C_4$haloalkyl, $C_1$-$C_4$alkoxy-, $C_1$-$C_4$haloalkoxy- and —$S(O)_p$$C_1$-$C_4$alkyl;

$R^3$ is selected from the group consisting of hydrogen, halogen, $C_1$-$C_3$alkyl, $C_1$-$C_3$haloalkyl and $C_2$-$C_3$alkenyl;

$R^4$ is selected from the group consisting of hydrogen, halogen, $C_1$-$C_3$alkyl, $C_1$-$C_3$haloalkyl and $C_2$-$C_3$alkenyl;

n=0, 1 or 2; and p=0, 1 or 2.

$C_1$-$C_4$alkyl- includes, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu). $C_1$-$C_2$alkyl is methyl (Me, $CH_3$) or ethyl (Et, $C_2H_5$).

Halogen (or halo) includes, for example, fluorine, chlorine, bromine or iodine. The same correspondingly applies to halogen in the context of other definitions, such as haloalkyl.

$C_1$-$C_6$haloalkyl- includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoropropyl and 2,2,2-trichloroethyl, heptafluoro-n-propyl and perfluoro-n-hexyl. $C_1$-$C_4$haloalkyl- and $C_1$-$C_2$haloalkyl include, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, or 1,1-difluoro-2,2,2-trichloroethyl.

$C_1$-$C_4$alkoxy and $C_1$-$C_2$alkoxy includes, for example, methoxy and ethoxy.

$C_1$-$C_6$haloalkoxy- and $C_1$-$C_4$haloalkoxy- include, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_2$-$C_4$alkenyl- includes, for example, —CH═$CH_2$ (vinyl) and —$CH_2$—CH═$CH_2$ (allyl).

$C_2$-$C_4$alkynyl- refers to a straight or branched hydrocarbon chain radical group consisting solely of carbon and hydrogen atoms, containing at least one triple bond, having from two to four carbon atoms, and which is attached to the rest of the molecule by a single bond. Examples of $C_2$-$C_4$alkynyl include, but are not limited to, prop-1-ynyl, propargyl (prop-2-ynyl), and but-1-ynyl.

$C_1$-$C_4$alkyl-S— (alkylthio) includes, for example, methylthio, ethylthio, propylthio, isopropylthio, n-butylthio, isobutylthio, sec-butylthio or tert-butylthio, preferably methylthio or ethylthio.

$C_1$-$C_4$alkyl-S(O)— (alkylsulfinyl) includes, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_4$alkyl-$S(O)_2$— (alkylsulfonyl) includes, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In one embodiment of the present invention there is provided a compound of Formula (I) wherein Q is $C_1$-$C_6$fluoroalkyl.

In another embodiment of the present invention there is provided a compound of Formula (I) wherein Q is $C_1$-$C_6$fluoroalkyl-C(O)—.

In another embodiment of the present invention there is provided a compound of Formula (I) wherein Q is $C_1$-$C_6$haloalkoxy- (e.g $CF_3CH_2CH_2O$—).

In another embodiment of the present invention there is provided a compound of Formula (I) wherein Q is $C_1$-$C_6$haloalkoxyC(O)— (e.g $CF_3CH_2OC(O)$—).

In another embodiment of the present invention there is provided a compound of Formula (I) wherein Q is a 5-membered aromatic heterocyclic ring which is optionally substituted by 1 or 2 $R^2$ substituents independently selected from the group consisting of $C_1$-$C_4$alkyl, $C_2$-$C_4$alkenyl, $C_2$-$C_4$alkynyl, cyclopropyl, $C_1$-$C_4$haloalkyl, $C_1$-$C_2$alkoxy-, $C_1$-$C_2$haloalkoxy-, halogen, —C(O)$C_1$-$C_4$alkyl, $NO_2$, —$CH_2$CN, —CN and —$S(O)_p$$C_1$-$C_4$alkyl;

In a preferred embodiment of the present invention there is provided a compound of Formula (I) wherein Q is selected from the group consisting of:

(Q1)

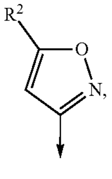

-continued (Q2)

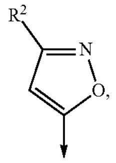

(Q3)

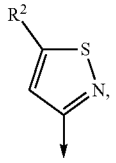

(Q4)

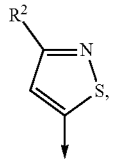

(Q5)

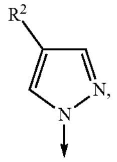

and (Q6)

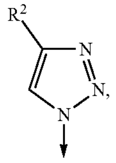

wherein $R^2$ is selected from the group consisting of hydrogen, $C_1$-$C_4$alkyl, $C_2$-$C_4$alkenyl, $C_2$-$C_4$alkynyl, cyclopropyl, $C_1$-$C_2$haloalkyl, $C_1$-$C_2$alkoxy-, $C_1$-$C_2$haloalkoxy-, halogen, —C(O)$C_1$-$C_4$alkyl, $NO_2$, —$CH_2$CN, —CN and —$S(O)_p C_1$-$C_4$alkyl.

In a more preferred embodiment of the present invention there is provided a compound of Formula (I), wherein Q is selected from the group consisting of Q1, Q2 and Q5, more preferably Q2.

In a preferred embodiment $R^2$ is $C_1$-$C_2$haloalkyl. In a more preferred embodiment $R^3$ is difluoromethyl or trifluoromethyl.

In one embodiment of the present invention, n is 1 and $R^1$ is selected from the group consisting of fluoro, chloro, bromo and CN. In a more preferred embodiment n is 1 and the $R^1$ substituent is present in the 3-position. In an even more preferred embodiment $R^1$ is 3-CN or 3-fluoro.

In another embodiment of the present invention there is provided a compound of Formula (I), wherein $R^3$ is selected from the group consisting of hydrogen, chloro, bromo and difluoromethyl In another embodiment of the present invention there is provided a compound of Formula (I), wherein $R^4$ is selected from the group consisting of hydrogen, chloro, bromo, methyl, vinyl and difluoromethyl.

Thus, in a preferred embodiment of the present invention the compound of Formula (I) is a compound of Formula (Ia):

(Ia)

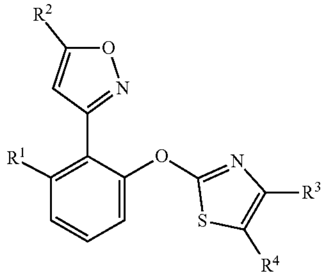

wherein $R^1$ is selected from the group consisting of hydrogen, fluoro, chloro and bromo, $R^2$ is $CF_3$ or —$CF_2$H, $R^3$ is selected from the group consisting hydrogen, Cl, Br and $CF_2$H and $R^4$ is selected from the group consisting hydrogen, Cl, Br and $CF_2$H.

In another preferred embodiment of the present invention the compound of Formula (I) is a compound of Formula (Ib):

(Ib)

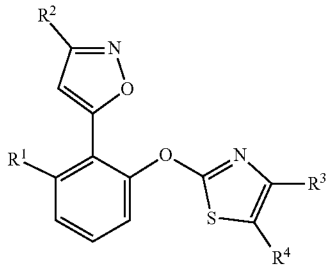

wherein $R^1$ is selected from the group consisting of hydrogen, fluoro, chloro and bromo, $R^2$ is $CF_3$ or $CF_2$H, $R^3$ is selected from the group consisting hydrogen, Cl, Br and $CF_2$H and $R^4$ is selected from the group consisting hydrogen, Cl, Br and $CF_2$H.

In another preferred embodiment of the present invention the compound of Formula (I) is a compound of Formula (Ic):

(Ic)

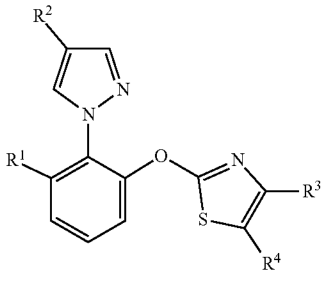

wherein $R^1$ is selected from the group consisting of hydrogen, fluoro, chloro and bromo, $R^2$ is $CF_3$ or $CF_2$H, $R^3$ is selected from the group consisting hydrogen, Cl, Br and $CF_2$H and $R^4$ is selected from the group consisting hydrogen, Cl, Br and $CF_2$H.

Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

The present invention also provides agronomically acceptable salts of compounds of Formula (I). Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred.

The compounds of Formula (I) according to the invention can be used as herbicides by themselves, but they are generally formulated into herbicidal compositions using formulation adjuvants, such as carriers, solvents and surface-active agents (SAA). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types. These include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a soluble powder (SP), a wettable powder (WP) and a soluble granule (SG). The formulation type chosen in any instance will depend upon the particular purpose envisaged and the physical, chemical and biological properties of the compound of Formula (I).

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SAAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SAAs, to produce spontaneously a thermodynamically stable isotropic liquid formulation. A compound of Formula (I) is present initially in either the water or the solvent/SAA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SAAs), spray additives based on oils, for example certain mineral oils or natural plant oils (such as soy bean and rape seed oil), modified plant oils such as methylated rape seed oil (MRSO), and blends of these with other bio-enhancing adjuvants (ingredients which may aid or modify the action of a compound of Formula (I).

Wetting agents, dispersing agents and emulsifying agents may be SAAs of the cationic, anionic, amphoteric or non-ionic type.

Suitable SAAs of the cationic type include quaternary ammonium compounds (for example cetyltrimethyl ammonium bromide), imidazolines and amine salts.

Suitable anionic SAAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates, lignosulphonates and phosphates/sulphates of tristyrylphenols.

Suitable SAAs of the amphoteric type include betaines, propionates and glycinates.

Suitable SAAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); lecithins and sorbitans and esters thereof, alkyl polyglycosides and tristyrylphenols.

Suitable suspending agents include hydrophilic colloids (such as polysaccharides, polyvinylpyrrolidone or sodium carboxymethylcellulose) and swelling clays (such as bentonite or attapulgite).

The herbicidal compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, beflubutamid-M, bensulfuron (including bensulfuron-methyl), bentazone, bicyclopyrone, bilanafos, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chlorotoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, diquat dibromide, diuron, ethalfluralin, ethofumesate, fenoxaprop (including fenoxaprop-P-ethyl), fenoxasulfone, fenquinotrione, fentrazamide, flazasulfuron, florasulam, florpyrauxifen (including florpyrauxifen-benzyl), fluazifop (including fluazifop-P-butyl), flucarbazone (including flucarbazone-sodium), flufenacet, flumetsulam, flumioxazin, fluometuron, flupyrsulfuron (including flupyrsulfuron-methyl-sodium), fluroxypyr (including fluroxypyr-meptyl), fomesafen, foramsulfuron, glufosinate (including the ammonium salt thereof), glyphosate (including the diammonium, isopropylammonium and potassium salts thereof), halauxifen (including halauxifen-methyl), haloxyfop (including haloxyfop-methyl), hexazinone, hydantocidin, imazamox, imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, prometryne, propanil, propaquizafop, propyrisulfuron, propyzamide, prosulfocarb, prosulfuron, pyraclonil, pyraflufen (including pyraflufen-ethyl), pyrasulfotole, pyridate, pyriftalid, pyrimisulfan, pyroxasulfone, pyroxsulam, quinclorac, quinmerac, quizalofop (including quizalofop-P-ethyl and quizalofop-P-tefuryl), rimsulfuron, saflufenacil, sethoxydim, simazine, S-metalochlor, sulfentrazone, sulfosulfuron, tebuthiuron, tefuryltrione, tembotrione, terbuthylazine, terbutryn, tetflupyrolimet, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, ethyl 2-[[3-[2-chloro-4-fluoro-5-[3-methyl-2,6-dioxo-4-(trifluoromethyl)pyrimidin-1-yl]phenoxy]-2-pyridyl]oxy]acetate, 3-(2-chloro-4-fluoro-5-(3-methyl-2,6-dioxo-4-trifluoromethyl-3,6-dihydropyrimidin-1(2H)-yl)phenyl)-5-methyl-4,5-dihydroisoxazole-5-carboxylic acid ethyl ester, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl]imidazolidin-2-one, (4R)1-(5-tert-butylisoxazol-3-yl)-4-ethoxy-5-hydroxy-3-methyl-imidazolidin-2-one, 3-[2-(3,4-dimethoxyphenyl)-6-methyl-3-oxo-pyridazine-4-carbonyl]bicyclo[3.2.1]octane-2,4-dione, 2-[2-(3,4-dimethoxyphenyl)-6-methyl-3-oxo-pyridazine-4-carbonyl]-5-methyl-cyclohexane-1,3-dione, 2-[2-(3,4-dimethoxyphenyl)-6-methyl-3-oxo-pyridazine-4-carbonyl]cyclohexane-1,3-dione, 2-[2-(3,4-dimethoxyphenyl)-6-methyl-3-oxo-pyridazine-4-carbonyl]-5,5-dimethyl-cyclohexane-1,3-dione, 6-[2-(3,4-dimethoxyphenyl)-6-methyl-3-oxo-pyridazine-4-carbonyl]-2,2,4,4-tetramethyl-cyclohexane-1,3,5-trione, 2-[2-(3,4-dimethoxyphenyl)-6-methyl-3-oxo-pyridazine-4-carbonyl]-5-ethyl-cyclohexane-1,3-dione, 2-[2-(3,4-dimethoxyphenyl)-6-methyl-3-oxo-pyridazine-4-carbonyl]-4,4,6,6-tetramethyl-cyclohexane-1,3-dione, 2-[6-cyclopropyl-2-(3,4-dimethoxyphenyl)-3-oxo-pyridazine-4-carbonyl]-5-methyl-cyclohexane-1,3-dione, 3-[6-cyclopropyl-2-(3,4-dimethoxyphenyl)-3-oxo-pyridazine-4-carbonyl]bicyclo[3.2.1]octane-2,4-dione, 2-[6-cyclopropyl-2-(3,4-dimethoxyphenyl)-3-oxo-pyridazine-4-carbonyl]-5,5-dimethyl-cyclohexane-1,3-dione, 6-[6-cyclopropyl-2-(3,4-dimethoxyphenyl)-3-oxo-pyridazine-4-carbonyl]-2,2,4,4-tetramethyl-cyclohexane-1,3,5-trione, 2-[6-cyclopropyl-2-(3,4-dimethoxyphenyl)-3-oxo-pyridazine-4-carbonyl]cyclohexane-1,3-dione, 4-[2-(3,4-dimethoxyphenyl)-6-methyl-3-oxo-pyridazine-4-carbonyl]-2,2,6,6-tetramethyl-tetrahydropyran-3,5-dione, 4-[6-cyclopropyl-2-(3,4-dimethoxyphenyl)-3-oxo-pyridazine-4-carbonyl]-2,2,6,6-tetramethyl-tetrahydropyran-3,5-dione and 4-amino-3-chloro-5-fluoro-6-(7-fluoro-1H-indol-6-yl)pyridine-2-carboxylic acid (including agrochemically acceptable esters thereof, for example, methyl 4-amino-3-chloro-5-fluoro-6-(7-fluoro-1H-indol-6-yl)pyridine-2-carboxylate).

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil.

Particularly preferred are mixtures of a compound of Formula (I) with cyprosulfamide, isoxadifen-ethyl, cloquintocet-mexyl and/or metcamifen.

The safeners of the compound of Formula (I) may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048.

Preferably the mixing ratio of compound of Formula (I) to safener is from 100:1 to 1:10, especially from 20:1 to 1:1.

The present invention still further provides a method of controlling weeds at a locus said method comprising application to the locus of a weed controlling amount of a composition comprising a compound of Formula (I). Moreover, the present invention may further provide a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. It is noted that the compounds of the present invention show a much improved selectivity compared to know, structurally similar compounds. Generally the plants to be controlled are unwanted plants (weeds). 'Locus' means the area in which the plants are growing or will grow. The application may be applied to the locus pre-emergence and/or postemergence of the crop plant. Some crop plants may be inherently tolerant to herbicidal effects of compounds of Formula (I). Preferred crop plants include maize, wheat, barley and rice.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2500 g/ha, especially from 25 to 1000 g/ha, more especially from 25 to 250 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to other herbicides or classes of herbicides (e.g. ALS-, GS-, EPSPS-, PPO-, HPPD-, -PDS and ACCase-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK®

(Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and Sorghum, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium.*

In a further aspect of the present invention there is provided the use of a compound of Formula (I) as defined herein as a herbicide.

The compounds of the present invention can be prepared according to the following schemes.

Processes for preparation of compounds, e.g. a compound of formula (I) (which optionally can be an agrochemically acceptable salt thereof), are now described, and form further aspects of the present invention.

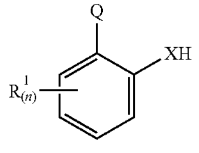

Formula A

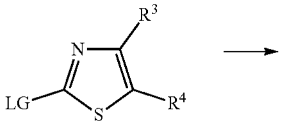

Formula B

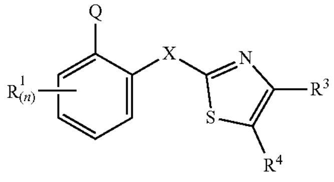

Formula I

A compound of Formula I may be prepared from a compound of Formula A by reaction with a compound of Formula B (where LG represents a suitable leaving group such as Br, Cl, F or $SO_2Me$) optionally in the presence of a suitable base and/or in the presence of a suitable catalyst and in a suitable solvent at a suitable reaction temperature. Suitable bases may include $K_2CO_3$ or $Cs_2CO_3$. Suitable catalysts may include Cu(I)I. Suitable solvents may include DMF. Suitable reaction temperatures may be between 20° C. and 130° C. Compounds of Formula A and of Formula B are commercially available or may be prepared by methods described in the literature.

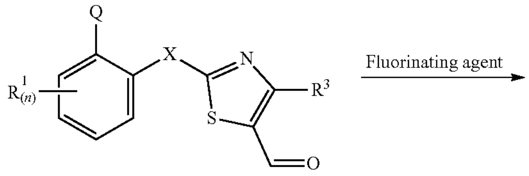

Formula C

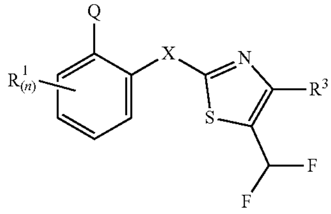

Formula Ia-1

Alternatively, a compound of Formula Ia-1 (a compound of Formula 1 where $R^4$=$CF_2H$) may be prepared by reaction of a compound of Formula C with a suitable fluorinating reagent in a suitable solvent. Suitable fluorinating reagents may include bis(2-methoxyethyl)aminosulfur trifluoride (Deoxo-Fluor®) and suitable solvents may include DCM.

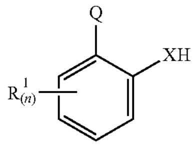

Formula A

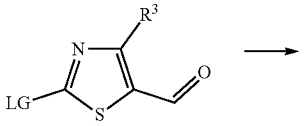

Formula D

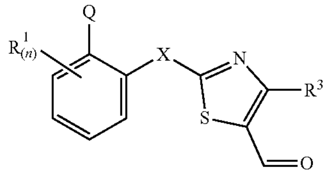

Formula IC

A compound of Formula C may be prepared from a compound of Formula A by reaction with a compound of Formula B (where LG represents a suitable leaving group such as Br, Cl, F or $SO_2Me$) optionally in the presence of a suitable base and in a suitable solvent at a suitable reaction temperature. Suitable bases may include $K_2CO_3$ or $Cs_2CO_3$. Suitable solvents may include DMF. Suitable reaction temperatures may be between 20° C. and 130° C. Compounds of Formula A and of Formula D are commercially available or may be prepared by methods described in the literature.

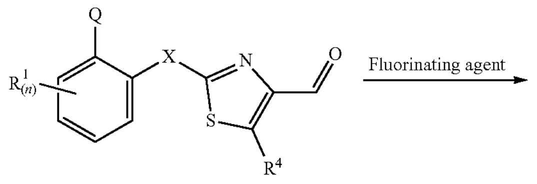

Formula E

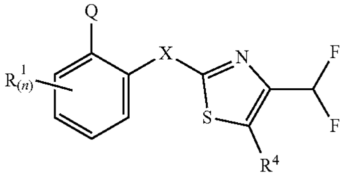

Formula Ib

In an analogous fashion, a compound of Formula Ib (a compound of Formula I where $R^3$=$CF_2H$) may be prepared by reaction of a compound of Formula E with a suitable fluorinating reagent in a suitable solvent. Suitable fluorinating reagents may include bis(2-methoxyethyl)aminosulfur trifluoride (Deoxo-Fluor®) and suitable solvents may include DCM.

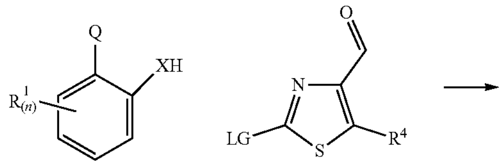

Formula A Formula F

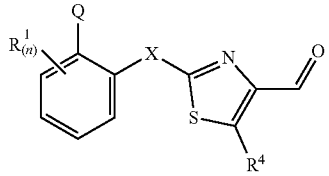

Formula E

A compound of Formula E may be prepared from a compound of Formula A by reaction with a compound of Formula F (where LG represents a suitable leaving group such as Br, Cl, F or $SO_2Me$) optionally in the presence of a suitable base and in a suitable solvent at a suitable reaction temperature. Suitable bases may include $K_2CO_3$ or $Cs_2CO_3$. Suitable solvents may include DMF. Suitable reaction temperatures may be between 20° C. and 130° C. Compounds of Formula A and of Formula F are commercially available or may be prepared by methods described in the literature.

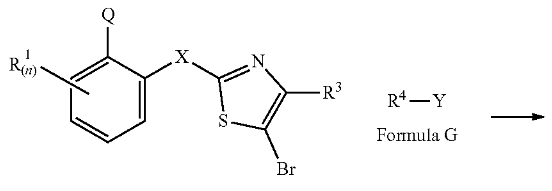

Formula Id $R^4$—Y

Formula G

-continued

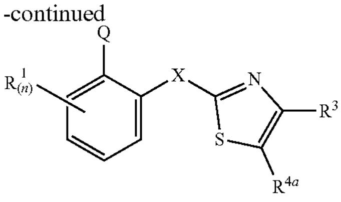

Formula Ic

A compound of Formula Ic (a compound of Formula I where $R^4$=$C_{1-3}$ alkyl or $C_{2-3}$ alkenyl) may be prepared from a compound of Formula Id (a compound of Formula I where $R^4$=Br) via a cross-coupling reaction with a compound of Formula G (where Y is a suitable coupling partner functional group, such as $B(OR)_2$ or $SnR_3$) in the presence of a suitable catalyst/ligand combination, optionally in the presence of a suitable base and in a suitable solvent. Suitable catalyst/ligand combinations may include [1,1'-bis(diphenylphosphino)ferrocene]dichloropalladium(II)(DCM complex) or tetrakis(triphenylphosphine)palladium(0). Suitable bases may include CsF or $K_2CO_3$. Suitable solvents may include 1,4-dioxane, water or mixtures thereof. Compounds of Formula G are commercially available or may be prepared by methods described in the literature.

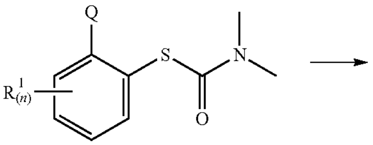

Formula H

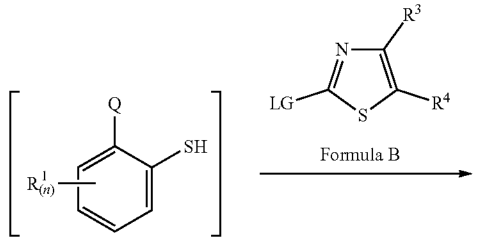

Formula B

Formula Aa

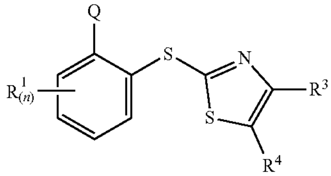

Formula Ia

In an alternative process, a compound of Formula Ia (a compound of Formula 1 where X=S) may be prepared from a compound of Formula H via a deprotection reaction and an $S_NAr$ reaction with a compound of Formula B. The intermediate compound of Formula Aa (a compound of Formula A where X=S) may be isolated or used in situ. Suitable deprotection conditions may include KOH in MeOH. Suitable conditions for the $S_NAr$ may include KOH in MeOH or $Cs_2CO_3$ or $K_2CO_3$ in DMF. Compounds of Formula B are commercially available or may be prepared by known methods.

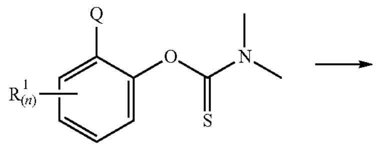

Formula J

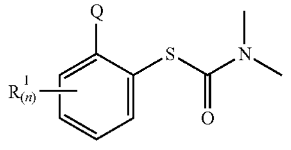

Formula H

A compound of Formula H may be prepared from a compound of Formula J via a Newman-Kwart rearrangement in a suitable solvent. Suitable solvents may include DMA.

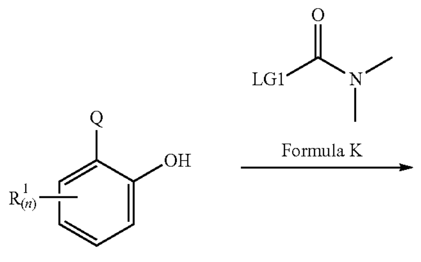

Formula K

Formula Ab

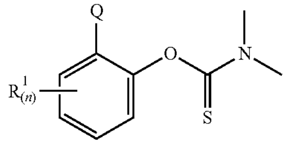

Formula J

A compound of Formula J may be prepared from a compound of Formula Ab (a compound of Formula A where X═O) via reaction with a compound of Formula K (where LG1 represents a suitable leaving group such as Cl) with a suitable base and in a suitable solvent. Suitable bases may include KOH. Suitable solvents may include THF/$H_2O$. Compounds of Formula K are commercially available or may be prepared by known methods.

The following non-limiting examples provide specific synthesis methods for representative compounds of the present invention, as referred to in the Table below.

EXAMPLE 1: SYNTHESIS OF 3-(DIFLUOROMETHYL)-5-[2-[5-(DIFLUOROMETHYL)THIAZOL-2-YL]OXY-6-FLUORO-PHENYL]ISOXAZOLE (1.001)

Step 1: Synthesis of 2-[2-[3-(difluoromethyl)isoxazol-5-yl]-3-fluoro-phenoxy]thiazole-5-carbaldehyde

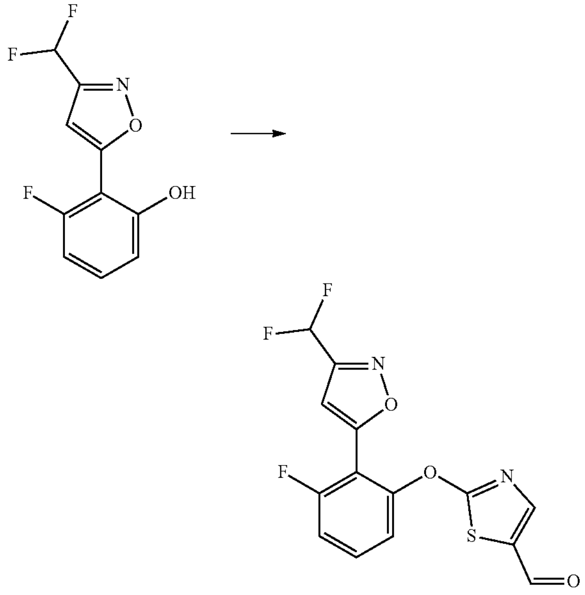

A solution of 2-[3-(difluoromethyl)isoxazol-5-yl]-3-fluoro-phenol (300 mg, 1.3 mmol), 2-chlorothiazole-5-carbaldehyde (230 mg, 1.6 mmol) and $K_2CO_3$ (900 mg, 6.4 mmol) in DMF (10 mL) was stirred at RT for 1 hour. The reaction was diluted with water and extracted with $Et_2O$. The organic extracts were washed with water, dried over $MgSO_4$ and evaporated to dryness under reduced pressure. The crude product was purified by flash chromatography on silica gel using a gradient of EtOAc/cyclohexane as eluent to give the desired product (385 mg, 86%) as an off-white solid.

$^1H$ NMR (400 MHz, $CDCl_3$) δ 9.85 (s, 1H) 7.83 (s, 1H) 7.60 (td, 1H) 7.32-7.26 (m, 2H) 6.89 (d, 1H) 6.79 (t, 1H)

Step 2: Synthesis of 3-(difluoromethyl)-5-[2-[5-(difluoromethyl)thiazol-2-yl]oxy-6-fluoro-phenyl]isoxazole (1.001)

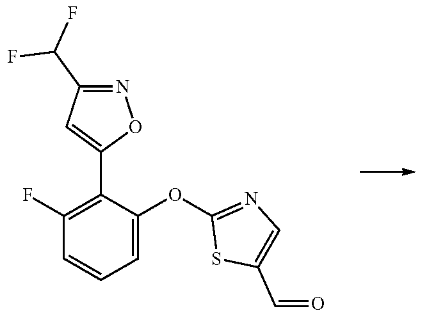

-continued

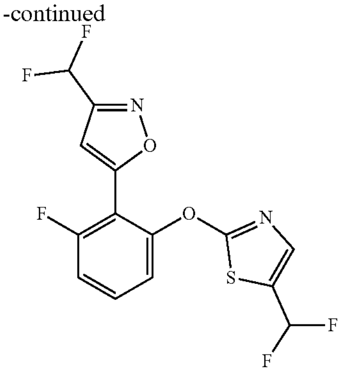

A solution of 2-[2-[3-(difluoromethyl)isoxazol-5-yl]-3-fluoro-phenoxy]thiazole-5-carbaldehyde (200 mg, 0.59 mmol) and bis(2-methoxyethyl)aminosulfur trifluoride (1.2 mL, 3.3 mmol) in DCM (10 mL) was heated at 80° C. for 30 mins under microwave irradiation. The reaction was cooled and then poured into satd. aq. $NaHCO_3$ solution and extracted with DCM. The organic extracts were washed with brine, dried over $MgSO_4$ and evaporated to dryness under reduced pressure. The crude product was purified by flash chromatography on silica gel using a gradient of EtOAc/cyclohexane as eluent to give the desired product (180 mg, 85%) as an off-white solid.

$^1H$ NMR (400 MHz, $CDCl_3$) δ 7.60-7.55 (m, 1H), 7.40-7.20 (m, 3H), 6.88 (d, 1H), 6.81 (t, 1H), 6.75 (t, 1H)

EXAMPLE 2: SYNTHESIS OF 5-[2-(5-BROMOTHIAZOL-2-YL)OXY-6-FLUORO-PHENYL]-3-(DIFLUOROMETHYL)ISOXAZOLE (1.004)

Step 1: Synthesis of 5-[2-(5-bromothiazol-2-yl)oxy-6-fluoro-phenyl]-3-(difluoromethyl)isoxazole (1.004)

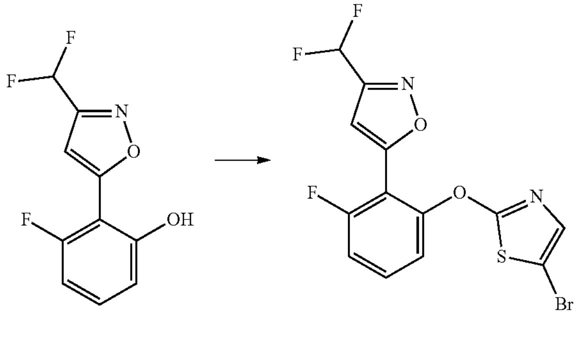 [SMILES: Oc1cccc(F)c1-c1cc(C(F)F)no1 ; Fc1cccc(Oc2ncc(Br)s2)c1-c1cc(C(F)F)no1]

A solution of 2-[3-(difluoromethyl)isoxazol-5-yl]-3-fluoro-phenol (1.0 g, 4.4 mmol), 2,5-dibromothiazole (1.25 g, 5.15 mmol), $K_2CO_3$ (3.0 g, 21 mmol) and copper(I) iodide (250 mg, 1.3 mmol) in DMF (35 mL) were heated at 130° C. for 3 hrs. The reaction was cooled, diluted with water and extracted with $Et_2O$. The organic extracts were washed with water, dried over $MgSO_4$ and evaporated to dryness under reduced pressure. The crude product was purified by flash chromatography on silica gel using a gradient of EtOAc/cyclohexane as eluent to give the desired product (900 mg, 53%) as an off-white solid.

$^1H$ NMR (400 MHz, $CDCl_3$) δ 7.53 (q, 1H), 7.25 (d, 1H), 7.18 (t, 1H), 7.11 (s, 1H), 6.87 (s, 1H), 6.80 (t, 1H)

EXAMPLE 3: SYNTHESIS OF 3-(DIFLUOROMETHYL)-5-[2-FLUORO-6-(5-VINYLTHIAZOL-2-YL)OXY-PHENYL]ISOXAZOLE (1.002)

Step 1: Synthesis of 3-(difluoromethyl)-5-[2-fluoro-6-(5-vinylthiazol-2-yl)oxy-phenyl]isoxazole (1.002)

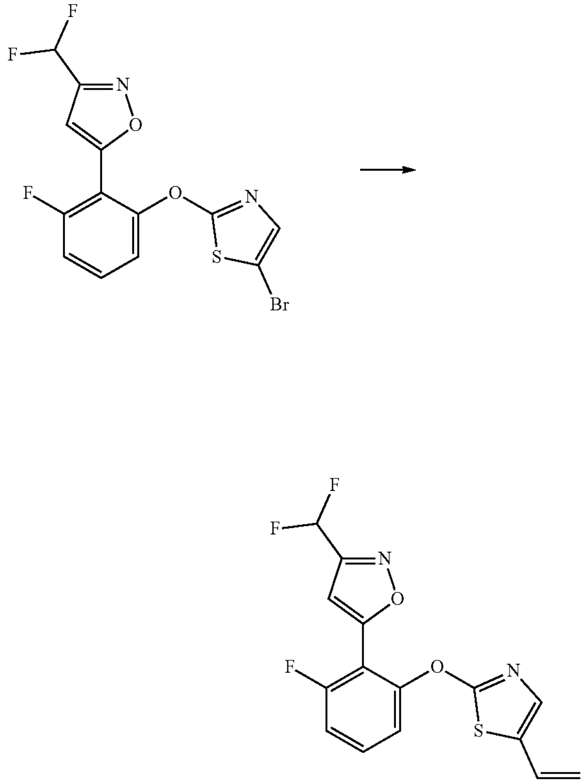

A solution of 5-[2-(5-bromothiazol-2-yl)oxy-6-fluoro-phenyl]-3-(difluoromethyl)isoxazole (100 mg, 0.26 mmol), vinyl boronic acid pinacol ester (45 mg, 0.29 mmol), CsF (80 mg, 0.53 mmol) and [1,1'-bis(diphenylphosphino)ferrocene]dichloropalladium(II), complex with dichloromethane (10 mg, 0.012 mmol) in a mixture of 1,4-dioxane (2 mL) and water (0.5 mL) was heated at 150° C. for 30 mins under microwave irradiation. The reaction was cooled, diluted with water and extracted with $Et_2O$. The organic extracts were washed with water, dried over $MgSO_4$ and evaporated to dryness under reduced pressure. The crude product was purified by flash chromatography on silica gel using a gradient of EtOAc/cyclohexane as eluent to give the desired product (65 mg, 75%) as an off-white solid.

$^1H$ NMR (400 MHz, $CDCl_3$) δ 7.57-7.52 (m, 1H), 7.29 (d, 1H), 7.18 (t, 1H), 7.02 (s, 1H), 6.88 (d, 1H), 6.81 (t, 1H), 6.66 (dd, 1H), 5.37 (d, 1H), 5.19 (d, 1H)

EXAMPLE 4: SYNTHESIS OF 3-(DIFLUOROMETHYL)-5-[2-FLUORO-6-(5-METHYLTHIAZOL-2-YL)OXY-PHENYL]ISOXAZOLE (1.005)

Step 1: Synthesis of 3-(difluoromethyl)-5-[2-fluoro-6-(5-methylthiazol-2-yl)oxy-phenyl]isoxazole (1.005)

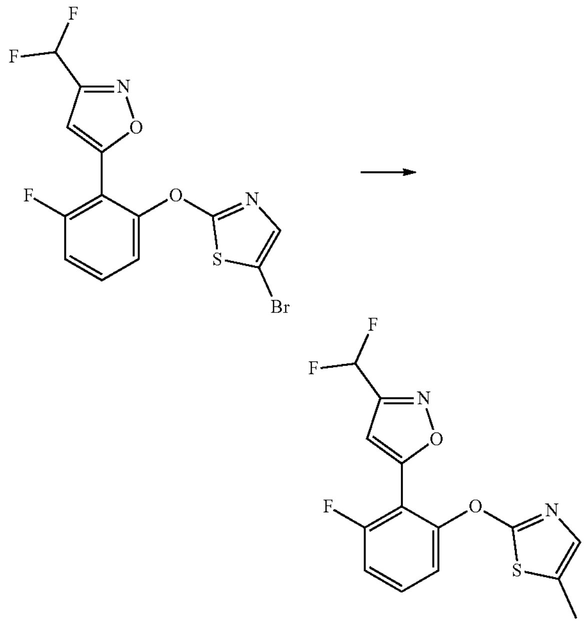

A solution of 5-[2-(5-bromothiazol-2-yl)oxy-6-fluoro-phenyl]-3-(difluoromethyl)isoxazole (100 mg, 0.26 mmol), trimethylboroxine (40 mg, 0.32 mmol), $K_2CO_3$ (180 mg, 1.30 mmol) and tetrakis(triphenylphosphine)palladium(0) (30 mg, 0.026 mmol) in a mixture of 1,4-dioxane (2 mL), and water (0.5 mL) were heated at 150° C. for 30 mins under microwave irradiation. The reaction was cooled, diluted with water and extracted with $Et_2O$. The organic extracts were washed with water, dried over $MgSO_4$ and evaporated to dryness under reduced pressure. The crude product was purified by flash chromatography on silica gel using gradient of EtOAc/cyclohexane as eluent to give the desired product (45 mg, 54%) as a pale yellow oil.

$^1$H NMR (400 MHz, $CDCl_3$) δ 7.54-7.50 (m, 1H), 7.25 (d, 1H), 7.14 (t, 1H), 6.87 (s, 1H), 6.84 (s, 1H), 6.81 (t, 1H), 2.37 (s, 3H)

EXAMPLE 5: SYNTHESIS OF 5-[2-(5-CHLOROTHIAZOL-2-YL)SULFANYL-6-FLUORO-PHENYL]-3-(DIFLUOROMETHYL)ISOXAZOLE (1.031)

Step 1: Synthesis of O-[2-[3-(difluoromethyl)isoxazol-5-yl]-3-fluoro-phenyl] N,N-dimethylcarbamothioate To a stirred solution of KOH (0.288 g, 4.36 mmol) in water (10 mL) was added 2-[3-(difluoromethyl)isoxazol-5-yl]-3-fluoro-phenol (1.00 g, 4.36 mmol) followed by drop-wise addition of a solution of N,N-dimethylcarbamothioyl chloride (0.539 g, 4.36 mmol) in THF (4 mL). The reaction was stirred at RT for 10 minutes then dilute with 2M NaOH and extracted with DCM (x2). The combined organic extracts were washed with water, dried over $MgSO_4$ and evaporated to dryness under reduced pressure to give the desired product as a yellow solid $^1$H NMR (400 MHz, $CDCl_3$) δ 7.51 (td, 1H) 7.18 (ddd, 1H) 7.12-7.04 (m, 1H) 6.89 (d, 1H) 6.82 (t, 1H) 3.44 (s, 3H) 3.41 (s, 3H)

Step 2: Synthesis of S-[2-[3-(difluoromethyl)isoxazol-5-yl]-3-fluoro-phenyl] N,N-dimethylcarbamothioate A solution of O-[2-[3-(difluoromethyl)isoxazol-5-yl]-3-fluoro-phenyl] N,N-dimethylcarbamothioate (0.95 g, 3.0 mmol) in DMA (2 mL) was heated at 220° C. for 90 minutes under microwave irradiation. The reaction was allowed to cool to RT, diluted with water and extracted with $Et_2O$. The organic phase was dried over $MgSO_4$ and evaporated to dryness under reduced pressure. The crude product was purified by flash chromatography on silica gel using a gradient of 0-20% EtOAc/cyclohexane as eluent to give the desired product (0.58 g, 61%).

$^1$H NMR (400 MHz, $CDCl_3$) δ 7.55-7.45 (m, 2H), 7.32-7.23 (m, 1H), 6.83 (t, 1H), 6.72 (s, 1H), 3.00 (br, 6H)

Step 3: Synthesis of 5-[2-(5-chlorothiazol-2-yl)sulfanyl-6-fluoro-phenyl]-3-(difluoromethyl)isoxazole (B031)

To a stirred solution of S-[2-[3-(difluoromethyl)isoxazol-5-yl]-3-fluoro-phenyl] N,N-dimethylcarbamothioate (0.15 g, 0.47 mmol) in tetrahydrofuran (2.4 mL) were added KOH (0.06 g, 1.0 mmol) and MeOH (1.2 mL) and the reaction stirred at room temperature overnight. To the solution was then added 2-bromo-5-chlorothiazole (0.19 g, 0.95 mmol) and the reaction heated to 60° C. for 6 hours. The reaction was allowed to cool to RT, diluted with water and extracted with EtOAc. The organic phase was dried over $MgSO_4$ and evaporated to dryness under reduced pressure. The crude product was purified by flash chromatography on silica gel using a gradient of 0-50% EtOAc/cyclohexane as eluent to give the desired product (46 mg, 27%).

Purified by column chromatography. Fractions 8-9 were combined and concentrated to provide:

$^1$H NMR (400 MHz, $CDCl_3$) δ 7.55 (s, 1H), 7.54-7.47 (m, 1H), 7.46-7.40 (m, 1H), 7.29-7.21 (m, 1H), 6.82 (t, 1H), 6.78 (s, 1H)

TABLE 1

Examples of herbicidal compounds of the present invention.

(I)

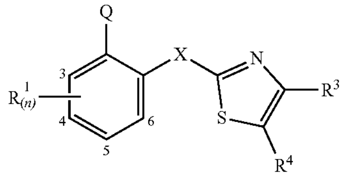

| CMP | n | $R^1$ | Q | X | $R^3$ | $R^4$ | $^1$H NMR (400 MHz, $CDCl_3$ unless stated) |
|---|---|---|---|---|---|---|---|
| 1.001 | 1 | 3-F | 5-(3-difluoro-methyl)-isoxazole | O | H | $CF_2H$ | 7.60-7.55 (m, 1H), 7.40-7.20 (m, 3H), 6.88 (d, 1H), 6.81 (t, 1H), 6.75 (t, 1H) |

TABLE 1-continued

Examples of herbicidal compounds of the present invention.

(I)

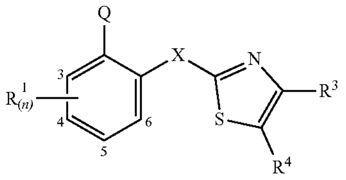

| CMP | n | $R^1$ | Q | X | $R^3$ | $R^4$ | $^1$H NMR (400 MHz, $CDCl_3$ unless stated) |
|---|---|---|---|---|---|---|---|
| 1.002 | 1 | 3-F | 5-(3-difluoro-methyl)-isoxazole | O | H | vinyl | 7.57-7.52 (m, 1H), 7.29 (d, 1H), 7.18 (t, 1H), 7.02 (s, 1H), 6.88 (d, 1H), 6.81 (t, 1H), 6.66 (dd, 1H), 5.37 (d, 1H), 5.19 (d, 1H) |
| 1.003 | 1 | 3-F | 5-(3-difluoro-methyl)-isoxazole | O | H | H | 7.56-7.52 (m, 1H), 7.29 (d, 1H), 7.20-7.15 (m, 2H), 6.92-6.87 (m, 2H), 6.80 (t, 1H) |
| 1.004 | 1 | 3-F | 5-(3-difluoro-methyl)-isoxazole | O | H | Br | 7.53 (q, 1H), 7.25 (d, 1H), 7.18 (t, 1H), 7.11 (s, 1H), 6.87 (s, 1H), 6.80 (t, 1H) |
| 1.005 | 1 | 3-F | 5-(3-difluoro-methyl)-isoxazole | O | H | $CH_3$ | 7.54-7.50 (m, 1H), 7.25 (d, 1H), 7.14 (t, 1H), 6.87 (s, 1H), 6.84 (s, 1H), 6.81 (t, 1H), 2.37 (s, 3H) |
| 1.006 | 1 | 3-F | 5-(3-difluoro-methyl)-isoxazole | O | H | Cl | 7.58-7.51 (m, 1H), 7.28 (d, 1H), 7.19 (t, 1H), 7.01 (s, 1H), 6.87 (s, 1H), 6.81 (t, 1H) |
| 1.007 | 1 | 3-F | 5-(3-difluoro-methyl)-isoxazole | O | Br | H | 7.59-7.50 (m, 1H), 7.29 (d, 1H), 7.20 (t, 1H), 7.11 (s, 1H), 6.88 (s, 1H), 6.81 (t, 1H) |
| 1.008 | 1 | 3-F | 5-(3-difluoro-methyl)-isoxazole | O | Cl | H | 7.58-7.52 (m, 1H), 7.30 (d, 1H), 7.21 (t, 1H), 6.88 (d, 1H), 6.81 (t, 1H), 6.65 (s, 1H) |
| 1.009 | 1 | 3-F | 5-(3-difluoro-methyl)-isoxazole | O | $CF_2H$ | H | 7.59-7.51 (m, 1H), 7.32 (d, 1H), 7.23-7.17 (m, 2H), 6.87 (s, 1H), 6.80 (t, 1H), 6.48 (t, 1H) |
| 1.010 | 1 | 6-F | 5-(3-difluoro-methyl)-isoxazole | O | H | Cl | 7.82 (td, 1H), 7.44 (dt, 1H), 7.40-7.31 (m, 1H), 6.99 (s, 1H), 6.84 (s, 1H), 6.80 (t, 1H) |
| 1.011 | 1 | 6-$CH_3$ | 5-(3-difluoro-methyl)-isoxazole | O | H | Cl | 7.87 (dd, 1H), 7.44 (d, 1H), 7.38 (t, 1H), 6.98 (s, 1H), 6.79 (s, 1H), 6.77 (t, 1H), 2.30 (s, 3H) |

TABLE 1-continued

Examples of herbicidal compounds of the present invention.

(I)

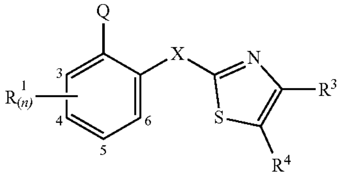

| CMP | n | $R^1$ | Q | X | $R^3$ | $R^4$ | $^1$H NMR (400 MHz, $CDCl_3$ unless stated) |
|---|---|---|---|---|---|---|---|
| 1.012 | 1 | 3-CN | 5-(3-difluoro-methyl)-isoxazole | O | H | Cl | 7.79-7.73 (m, 2H), 7.70-7.66 (m, 1H), 7.02 (s, 1H), 6.98 (s, H), 6.84 (t, 1H) |
| 1.013 | 1 | 3-CN | 5-(3-difluoro-methyl)-isoxazole | O | H | Br | 7.81-7.63 (m, 3H), 7.13 (s, 1H), 6.98 (s, 1H), 6.84 (t, 1H) |
| 1.014 | 1 | 3-CN | 5-(3-difluoro-methyl)-isoxazole | O | H | $CF_2H$ | 7.83-7.75 (m, 2H), 7.71 (t, 1H), 7.35 (t, 1H), 6.99 (s, 1H), 6.83 (t, 1H), 6.77 (t, 1H) |
| 1.015 | 1 | 3-CN | 4-(trifluoro-methyl) pyrazol-1-yl | O | H | Br | 8.01 (s, 1H), 7.98 (s, 1H), 7.80-7.72 (m, 2H), 7.65 (t, H), 7.08 (s, 1H) |
| 1.016 | 1 | 3-CN | 4-(trifluoro-methyl) pyrazol-1-yl | O | H | $CH_3$ | 8.01 (s, 1H), 7.98 (s, 1H), 7.72 (dd, 1H), 7.74 (dd, 1H), 7.62 (t, 1H), 6.81 (d, 1H), 2.35 (d, 3H) |
| 1.017 | 1 | 3-CN | 4-(trifluoro-methyl) pyrazol-1-yl | O | H | $CF_2H$ | 8.01 (s, 1H), 7.96 (s, 1H), 7.83-7.74 (m, 2H), 7.68 (t, 1H), 7.29 (t, 1H), 6.73 (t, 1H) |
| 1.018 | 1 | 3-CN | 4-(trifluoro-methyl) pyrazol-1-yl | O | H | Cl | 8.01 (s, 1H), 7.98 (s, 1H), 7.79-7.73 (m, 2H), 7.65 (t, 1H), 6.98 (s, 1H) |
| 1.019 | 1 | 3-Cl | 5-(3-difluoro-methyl)-isoxazole | O | H | $CF_2H$ | 7.57-7.49 (m, 2H), 7.40 (dd, 1H), 7.34 (t, 1H), 6.81 (t, 1H), 6.74 (t, 1H), 6.72 (s, 1H) |
| 1.020 | 1 | 3-Br | 5-(3-difluoro-methyl)-isoxazole | O | H | $CF_2H$ | 7.68 (dd, 1H), 7.51-7.42 (m, 2H), 7.34 (t, 1H), 6.80 (t, 1H), 6.74 (t, 1H), 6.67 (s, 1H) |
| 1.021 | 0 | — | 5-(3-difluoro-methyl)-isoxazole | O | H | $CF_2H$ | 8.07 (dd, 1H), 7.59 (t, 1H), 7.52-7.40 (m, 3H), 6.87 (s, 1H), 6.80 (t, 1H), 6.76 (t, 1H) |
| 1.022 | 1 | 3-Cl | 5-(3-difluoro-methyl)-isoxazole | O | H | Cl | 7.57-7.44 (m, 2H), 7.37 (d, 1H), 7.01 (s, 1H), 6.82 (t, 1H), 6.72 (s, 1H) |

TABLE 1-continued

Examples of herbicidal compounds of the present invention.

(I)

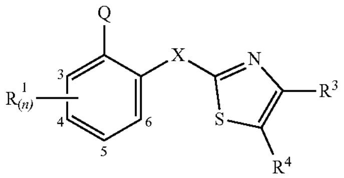

| CMP | n | $R^1$ | Q | X | $R^3$ | $R^4$ | $^1H$ NMR (400 MHz, $CDCl_3$ unless stated) |
|---|---|---|---|---|---|---|---|
| 1.023 | 1 | 3-Br | 5-(3-difluoro-methyl)-isoxazole | O | H | Cl | 7.65 (dd, 1H), 7.49-7.39 (m, 2H), 7.01 (s, 1H), 6.82 (t, 1H), 6.68 (s, 1H) |
| 1.024 | 1 | 3-Br | 5-(3-difluoro-methyl)-isoxazole | O | H | Br | 7.65 (dd, 1H), 7.49-7.38 (m, 2H), 7.11 (s, 1H), 6.82 (t, 1H), 6.67 (s, 1H) |
| 1.025 | 1 | 3-Cl | 5-(3-difluoro-methyl)-isoxazole | O | H | Br | 7.55-7.45 (m, 2H), 7.39-7.35 (m, 1H), 7.11 (s, 1H), 6.82 (t, 1H), 6.72 (s, 1H) |
| 1.026 | 0 | H | 5-(3-difluoro-methyl)-isoxazole | O | H | Cl | 8.06 (dd, 1H), 7.55 (t, 1H), 7.47-7.38 (m, 2H), 7.09 (s, 1H), 6.86 (s, 1H), 6.80 (t, 1H) |
| 1.027 | 0 | H | 5-(3-difluoro-methyl)-isoxazole | O | H | Br | 8.06 (dd, 1H), 7.55 (t, 1H), 7.47-7.39 (m, 2H), 7.19 (s, 1H), 6.88 (s, 1H), 6.80 (t, 1H) |
| 1.028 | 1 | 3-Br | 5-(3-difluoro-methyl)-isoxazole | O | Cl | Cl | 7.67 (dd, 1H), 7.49-7.40 (m, 2H), 6.82 (t, 1H), 6.71 (s, 1H) |
| 1.029 | 1 | 3-F | 5-(3-difluoro-methyl)-isoxazole | O | Cl | Cl | 7.55 (td, 1H), 7.29 (dt, 1H), 7.21 (ddd, 1H), 6.88 (d, 1H), 6.82 (t, 1H) |
| 1.030 | 1 | 3-Br | 5-(3-difluoro-methyl)-isoxazole | O | $CF_2H$ | Cl | 7.70 (dd, 1H), 7.52-7.41 (m, 2H), 6.82 (t, 1H), 6.81 (t, 1H), 6.71 (s, 1H) |
| 1.031 | 1 | 3-F | 5-(3-difluoro-methyl)-isoxazole | S | Cl | H | 7.55 (s, 1 H), 7.54-7.47 (m, 1H), 7.46-7.40 (m, 1H), 7.29-7.21 (m, 1H), 6.82 (t, 1H), 6.78 (s, 1H) |
| 1.032 | 1 | 3-Cl | 5-(3-difluoro-methyl)-isoxazole | O | Cl | Cl | 7.56-7.47 (m, 2H), 7.39 (dd, 1H), 6.82 (t, 1H), 6.75 (s, 1H) |
| 1.033 | 1 | 3-F | 5-(3-difluoro-methyl)-isoxazole | O | $CF_3$ | H | 7.58 (td, 1H), 7.51-7.47 (m, 1H), 7.31 (dt, 1H), 7.27-7.22 (m, 1H), 6.89 (d, 1H), 6.81 (t, 1H) |
| 1.034 | 1 | 3-Br | 5-(3-difluoro-methyl)-isoxazole | O | $CF_3$ | H | 7.70 (dd, 1H), 7.52-7.42 (m, 3H), 6.81 (t, 1H), 6.68 (s, 1H) |
| 1.035 | 1 | 3-F | 5-(3-difluoro-methyl)-isoxazole | O | $CF_2H$ | Cl | 7.58 (td, 1H), 7.30 (dt, 1H), 7.27-7.20 (m, 1H), 6.89 (d, 1H), 6.84 (t, 1H), 6.81 (t, 1H) |

BIOLOGICAL EXAMPLES

Seeds of a variety of test species are sown in standard soil in pots *Amaranthus retoflexus* (AMARE), *Echinochloa crus-galli* (ECHCG), *Setaria faberi* (SETFA)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween™ 20 (polyoxyethylene sorbitan monolaurate, CAS RN 9005-64-5). Compounds are applied at 250 g/ha unless otherwise stated. The test plants are then grown in a glasshouse under controlled conditions in a glasshouse (at 24/16° C., day/night; 14 hours light; 65% humidity) and watered twice daily. After 13 days for pre- and post-emergence, the test is evaluated for the percentage damage caused to the plant. The biological activities are shown in the following table on a five-point scale (5=81-100%; 4=61-80%; 3=41-60%; 2=21-40%; 1=0-20%).

TABLE B1

Post-emergence Test

| Compound | AMARE | ECHCG | SETFA |
|---|---|---|---|
| 1.001 | 5 | 5 | 5 |
| 1.002 | 2 | 4 | 4 |
| 1.003 | 2 | 1 | 2 |
| 1.004 | 5 | 5 | 5 |
| 1.005 | 4 | 4 | 4 |
| 1.006 | 5 | 4 | 5 |
| 1.007 | 5 | 4 | 5 |
| 1.008 | 4 | 2 | 1 |
| 1.009 | 4 | 2 | 2 |
| 1.010 | 4 | 3 | 4 |
| 1.011 | 2 | 3 | 3 |
| 1.012 | 5 | 3 | 4 |
| 1.013 | 5 | 2 | 3 |
| 1.014 | 3 | 3 | 4 |
| 1.019 | 4 | 4 | 5 |
| 1.020 | 4 | 4 | 5 |
| 1.021 | 4 | 1 | 3 |
| 1.022 | 5 | 5 | 5 |
| 1.023 | 5 | 5 | 5 |
| 1.024 | 5 | 5 | 5 |
| 1.025 | 5 | 5 | 5 |
| 1.026 | 4 | 4 | 4 |
| 1.028 | 4 | 4 | 4 |
| 1.029 | 5 | 1 | 2 |
| 1.030 | 1 | 1 | 1 |
| 1.031 | 4 | 2 | 3 |
| 1.032 | 5 | 2 | 4 |
| 1.033 | 4 | 4 | 4 |
| 1.034 | 4 | 3 | 4 |
| 1.035 | 2 | 1 | 1 |

TABLE B2

Pre-emergence Test

| Compound | AMARE | ECHCG | SETFA |
|---|---|---|---|
| 1.001 | 5 | 5 | 5 |
| 1.002 | 1 | 4 | 2 |
| 1.003 | 5 | 2 | 2 |
| 1.004 | 5 | 4 | 5 |
| 1.005 | 5 | 3 | 4 |
| 1.006 | 5 | 5 | 5 |
| 1.007 | 5 | 3 | 5 |
| 1.008 | 3 | 1 | 3 |
| 1.009 | 4 | 3 | 5 |
| 1.010 | 5 | 4 | 4 |
| 1.011 | 4 | 4 | 1 |
| 1.012 | 2 | 4 | 5 |
| 1.013 | 2 | 4 | 4 |
| 1.014 | 3 | 5 | 5 |

TABLE B2-continued

| Pre-emergence Test | | | |
|---|---|---|---|
| Compound | AMARE | ECHCG | SETFA |
| 1.019 | 2 | 5 | 5 |
| 1.020 | 1 | 5 | 5 |
| 1.021 | 3 | 4 | 4 |
| 1.022 | 5 | 5 | 5 |
| 1.023 | 5 | 5 | 5 |
| 1.024 | 4 | 5 | 4 |
| 1.025 | 5 | 5 | 5 |
| 1.026 | 4 | 4 | 4 |
| 1.028 | 2 | 4 | 4 |
| 1.029 | 5 | 1 | 2 |
| 1.030 | 1 | 1 | 1 |
| 1.031 | 3 | 2 | 2 |
| 1.032 | 5 | 1 | 1 |
| 1.033 | 5 | 4 | 5 |
| 1.034 | 4 | 3 | 5 |
| 1.035 | 1 | 1 | 1 |

The invention claimed is:

1. A compound of Formula (I):

(I)

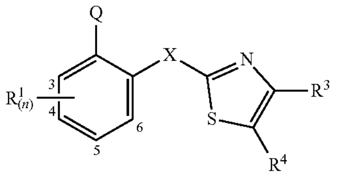

or an agronomically acceptable salt thereof, wherein

Q is a 5-membered aromatic heterocyclic ring selected from the group consisting of:

(Q1)

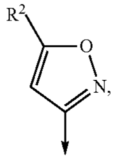

(Q2)

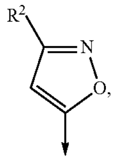

(Q3)

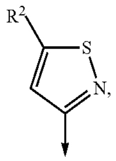

(Q4)

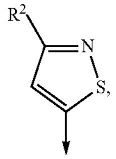

-continued (Q5)

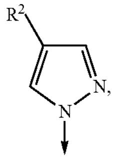

and (Q6)

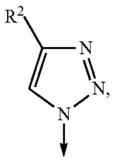

wherein $R^2$ is selected from the group consisting of hydrogen, $C_1$-$C_4$alkyl, $C_2$-$C_4$alkenyl, $C_2$-$C_4$alkynyl, cyclopropyl, $C_1$-$C_2$haloalkyl, $C_1$-$C_2$alkoxy-, $C_1$-$C_2$haloalkoxy-, halogen, —C(O)$C_1$-$C_4$alkyl, $NO_2$, —$CH_2$CN, —CN and —$S(O)_p C_1$-$C_4$alkyl;

X is O or $S(O)_p$;

each $R^1$ is independently selected from the group consisting of halogen, —CN, nitro, $C_1$-$C_4$alkyl, $C_2$-$C_4$alkenyl, $C_2$-$C_4$alkynyl, $C_1$-$C_4$haloalkyl, $C_1$-$C_4$alkoxy-, $C_1$-$C_4$haloalkoxy- and —$S(O)_p C_1$-$C_4$alkyl;

$R^3$ is selected from the group consisting of hydrogen, halogen, $C_1$-$C_3$alkyl, $C_1$-$C_3$haloalkyl and $C_2$-$C_3$alkenyl;

$R^4$ is selected from the group consisting of hydrogen, halogen, $C_1$-$C_3$alkyl, $C_1$-$C_3$haloalkyl and $C_2$-$C_3$alkenyl;

n=0, 1 or 2; and p=0, 1 or 2.

2. The compound of Formula (I) according to claim 1, wherein Q is selected from the group consisting of Q1, Q2 and Q5.

3. The compound of Formula (I) according to claim 1, wherein Q is Q2.

4. The compound according to claim 1, wherein n is 1 and $R^1$ is fluoro.

5. The compound according to claim 4, wherein $R^1$ is 3-fluoro.

6. The compound according to claim 1, wherein $R^3$ is selected from the group consisting of hydrogen, chloro, bromo and difluoromethyl.

7. The compound according to claim 1, wherein $R^4$ is selected from the group consisting of hydrogen, chloro, bromo, methyl, vinyl and difluoromethyl.

8. A herbicidal composition comprising a compound according to claim 1 and an agriculturally acceptable formulation adjuvant.

9. A herbicidal composition according to claim 8, further comprising at least one additional pesticide.

10. A herbicidal composition according to claim 9, wherein the additional pesticide is a herbicide.

11. A method of controlling weeds at a locus comprising application to the locus of a weed controlling amount of a composition according to claim 8.

12. A compound selected from Compound 1.001-1.035 according to Formula (I):

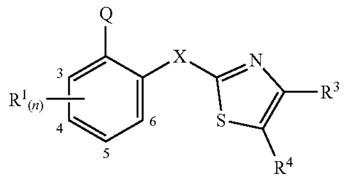

| CMP | n | $R^1$ | Q | x | $R^3$ | $R^4$ |
|---|---|---|---|---|---|---|
| 1.001 | 1 | 3-F | 5-(3 difluoromethyl)-isoxazole | O | H | $CF_2H$ |
| 1.002 | 1 | 3-F | 5-(3-difluoromethyl)-isoxazole | O | H | vinyl |
| 1.003 | 1 | 3-F | 5-(3-difluoromethyl)-isoxazole | O | H | H |
| 1.004 | 1 | 3-F | 5-(3. difluoromethyl)-isoxazole | O | H | Br |
| 1.005 | 1 | 3-F | 5-(3-difluoromethyl)-isoxazole | O | H | $CH_3$ |
| 1.006 | 1 | 3-F | 5-(3-difluoromethyl)-isoxazole | O | H | Cl |
| 1.007 | 1 | 3-F | 5-(3-difluoromethyl)-isoxazole | O | Br | H |
| 1.008 | 1 | 3-F | 5-(3-difluoromethyl)-isoxazole | O | Cl | H |
| 1.009 | | 3-F | 5-(3-difluoromethyl)-isoxazole | O | $CF_2H$ | H |
| 1.010 | 3 | 6-F | 5-(3-difluoromethyl)-isoxazole | O | H | Cl |
| 1.011 | 3 | $6-CH_3$ | 5-(3-difluoromethyl)-isoxazole | O | H | Cl |
| 1.012 | 3 | 3-CN | 5-(3-difluoromethyl)-isoxazole | O | H | Cl |
| 1.013 | 3 | 3-CN | 5-(3-difluoromethyl)-isoxazole | O | H | Br |
| 1.014 | 1 | 3-CN | 5-(3-difluoromethyl)-isoxazole | O | H | $CF_2H$ |
| 1.015 | 1 | 3-CN | 4-(vifluoromethyl) pyrazol-1-yl | O | H | Br |
| 1.016 | 1 | 3-CN | 4-(trifluoromethyl) pyrazol-1-yl | O | H | $CH_3$ |
| 1.017 | 1 | 3-CN | 4-(trifluoromethyl) pyrazol-1-yl | O | H | $CF_2H$ |
| 1.018 | 1 | 3-CN | 4-(trifluoromethyl) pyrazol-1-yl | O | H | Cl |
| 1.019 | 1 | 3-Cl | 5-(3-difluoromethyl) isoxazole | O | H | $CF_2H$ |
| 1.020 | 1 | 3-Br | 5-(3-difluoromethyl) isoxazole | O | H | $CF_2H$ |
| 1.021 | 0 | — | 5-(3-difluoromethyl) isoxazole | O | H | $CF_2H$ |
| 1.022 | 1 | 3-Cl | 5-(3-difluoromethyl) isoxazole | O | H | Cl |
| 1.023 | 1 | 3-Br | 5-(3-difluoromethyl) isoxazole | O | H | Cl |

-continued

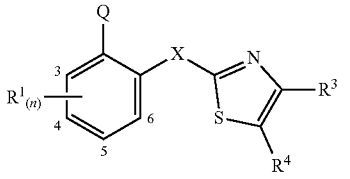

| CMP | n | $R^1$ | Q | x | $R^3$ | $R^4$ |
|---|---|---|---|---|---|---|
| 1.024 | 1 | 3-Br | 5-(3-difluoromethyl) isoxazole | O | H | Br |
| 1.025 | 1 | 3-Cl | 5-(3-difluoromethyl) isoxazole | O | H | Br |
| 1.026 | 0 | H | 5-(3-difluoromethyl) isoxazole | O | H | Cl |
| 1.027 | 0 | H | 5-(3-difluoromethyl) isoxazole | O | H | Br |
| 1.028 | 1 | 3-Br | 5-(3-difluoromethyl) isoxazole | O | Cl | Cl |
| 1.029 | 1 | 3-F | 5-(3-difluoromethyl) isoxazole | O | Cl | Cl |
| 1.030 | 1 | 3-Br | 5-(3-difluoromethyl) isoxazole | O | $CF_2H$ | Cl |
| 1.031 | 1 | 3-F | 5-(3-difluoromethyl) isoxazole | O | Cl | H |
| 1.032 | 1 | 3-Cl | 5-(3-difluoromethyl) isoxazole | O | Cl | Cl |
| 1.033 | 1 | 3-F | 5-(3-difluoromethyl) isoxazole | O | $CF_3$ | H |
| 1.034 | 1 | 3-Br | 5-(3-difluoromethyl) isoxazole | O | $CF_3$ | H |
| 1.035 | 1 | 3-F | 5-(3-difluoromethyl) isoxazole | O | $CF_3H$ | Cl. |

13. The compound according to claim 12, selected from:

3-(DIFLUOROMETHYL)-5-[2-[5-(DIFLUOROMETHYL) THIAZOL-2-YL]OXY-6-FLUORO-PHENYL]ISOXAZOLE (1.001);

5-[2-(5-BROMOTHIAZOL-2-YL)OXY-6-FLUORO-PHENYL]-3-(DIFLUOROMETHYL)ISOXAZOLE (1.004);

3-(DIFLUOROMETHYL)-5-[2-FLUORO-6-(5-VINYLTHIAZOL-2-YL)OXY-PHENYL]ISOXAZOLE (1.002);

3-(DIFLUOROMETHYL)-5-[2-FLUORO-6-(5-METHYLTHIAZOL-2-YL)OXY-PHENYL]ISOXAZOLE (1.005); and 5-[2-(5-CHLOROTHIAZOL-2-YL) SULFANYL-6-FLUORO-PHENYL]-3-(DIFLUOROMETHYL) ISOXAZOLE (1.031).

14. A herbicidal composition comprising a compound according to claim 12 and an agriculturally acceptable formulation adjuvant.

15. The herbicidal composition according to claim 14, further comprising at least one additional pesticide.

16. The herbicidal composition according to claim 14, further comprising at least one additional pesticide or a herbicide safener.

17. A method of controlling weeds at a locus comprising application to the locus of a weed controlling amount of the composition according to claim 14.

* * * * *